(12) United States Patent
Nakanishi et al.

(10) Patent No.: US 9,103,870 B2
(45) Date of Patent: Aug. 11, 2015

(54) INSPECTION APPARATUS AND INSPECTION METHOD

(71) Applicant: SCREEN HOLDINGS CO., LTD., Kyoto-shi, Kyoto (JP)

(72) Inventors: Hidetoshi Nakanishi, Kyoto (JP); Masayoshi Tonouchi, Suita (JP); Iwao Kawayama, Suita (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 267 days.

(21) Appl. No.: 13/744,987

(22) Filed: Jan. 18, 2013

(65) Prior Publication Data

US 2013/0222004 A1    Aug. 29, 2013

(30) Foreign Application Priority Data

Feb. 24, 2012    (JP) .................................. 2012-038272

(51) Int. Cl.
| | |
|---|---|
| G01R 31/00 | (2006.01) |
| G01R 31/26 | (2014.01) |
| G01N 21/95 | (2006.01) |
| H02S 50/10 | (2014.01) |

(52) U.S. Cl.
CPC ........ *G01R 31/2605* (2013.01); *G01N 21/9501* (2013.01); *H02S 50/10* (2014.12)

(58) Field of Classification Search
CPC ........... G01N 21/9501; G01N 21/3563; G01R 31/2605; G01R 31/311
USPC .................................. 324/754.23; 250/459.1
See application file for complete search history.

(56) References Cited

U.S. PATENT DOCUMENTS

| | | | |
|---|---|---|---|
| 4,389,085 A | * 6/1983 | Mori ............................. | 359/591 |
| 8,129,683 B2 | 3/2012 | Itsuji et al. | |
| 2006/0006886 A1 | 1/2006 | Yamashita et al. | |
| 2007/0218376 A1 | 9/2007 | Ouchi | |
| 2010/0201349 A1 | 8/2010 | Taira et al. | |
| 2011/0204909 A1* | 8/2011 | Buehler et al. ........... | 324/750.03 |
| 2011/0216312 A1 | 9/2011 | Matsumoto et al. | |

FOREIGN PATENT DOCUMENTS

| | | |
|---|---|---|
| EP | 1441233 A1 | 7/2004 |
| JP | 5 226431 A | 3/1993 |
| JP | 2009-175127 A | 8/2009 |
| JP | 2010-182969 A | 8/2010 |
| JP | 2011-155665 A | 8/2011 |

OTHER PUBLICATIONS

Extended European Seach Report for Application No. 13153055.2-1504 dated Mar. 21, 2013.

* cited by examiner

*Primary Examiner* — Vincent Q Nguyen
(74) *Attorney, Agent, or Firm* — McDermott Will & Emery LLP

(57) ABSTRACT

An inspection apparatus inspects a photovoltaic cell panel in which the photo device is formed. The inspection apparatus includes: an irradiation part that irradiates the photovoltaic cell panel with pulsed light (pump light) emitted from a femtosecond laser; a detecting part that detects an electromagnetic wave pulse, which is generated from the photovoltaic cell panel according to the irradiation of the pump light; and a continuous light irradiation part that irradiates a portion, which is irradiated with the pump light in the photovoltaic cell panel, with continuous light.

13 Claims, 13 Drawing Sheets

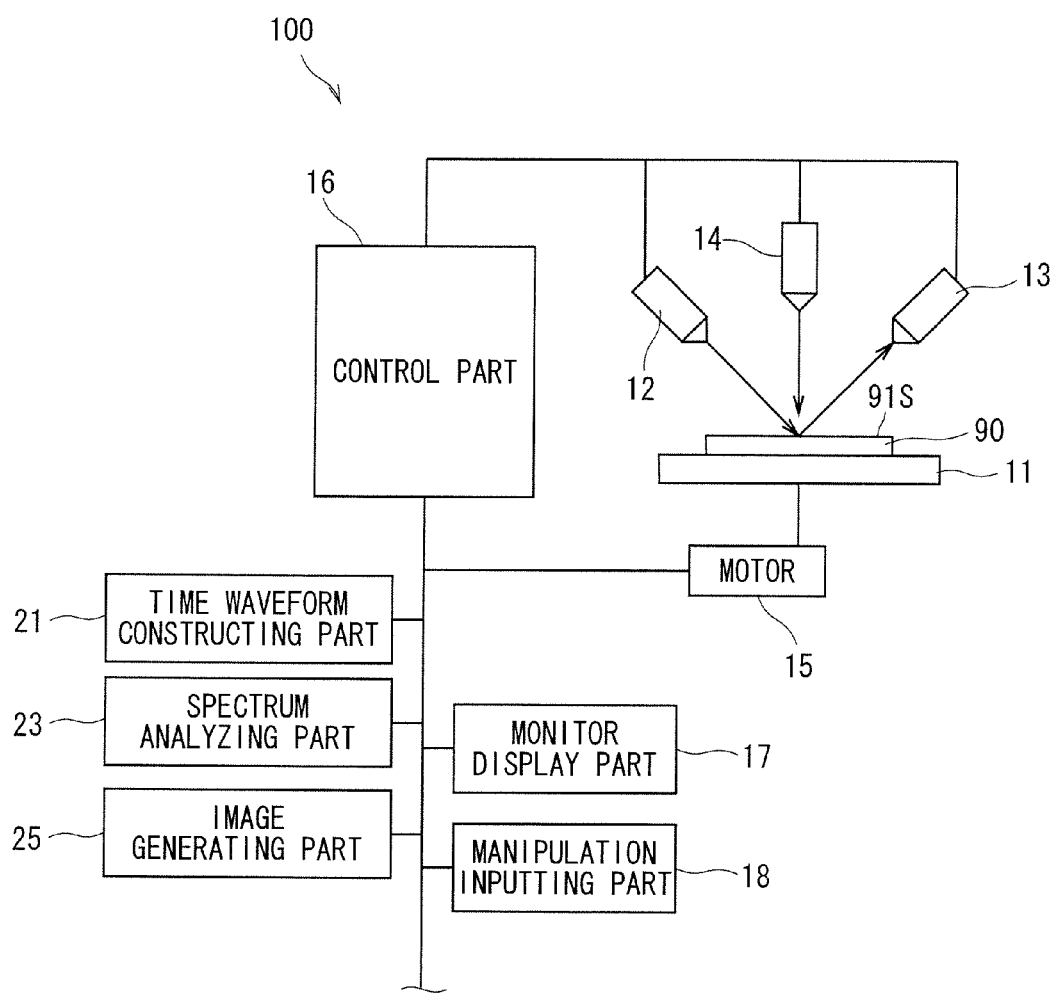
F I G . 1

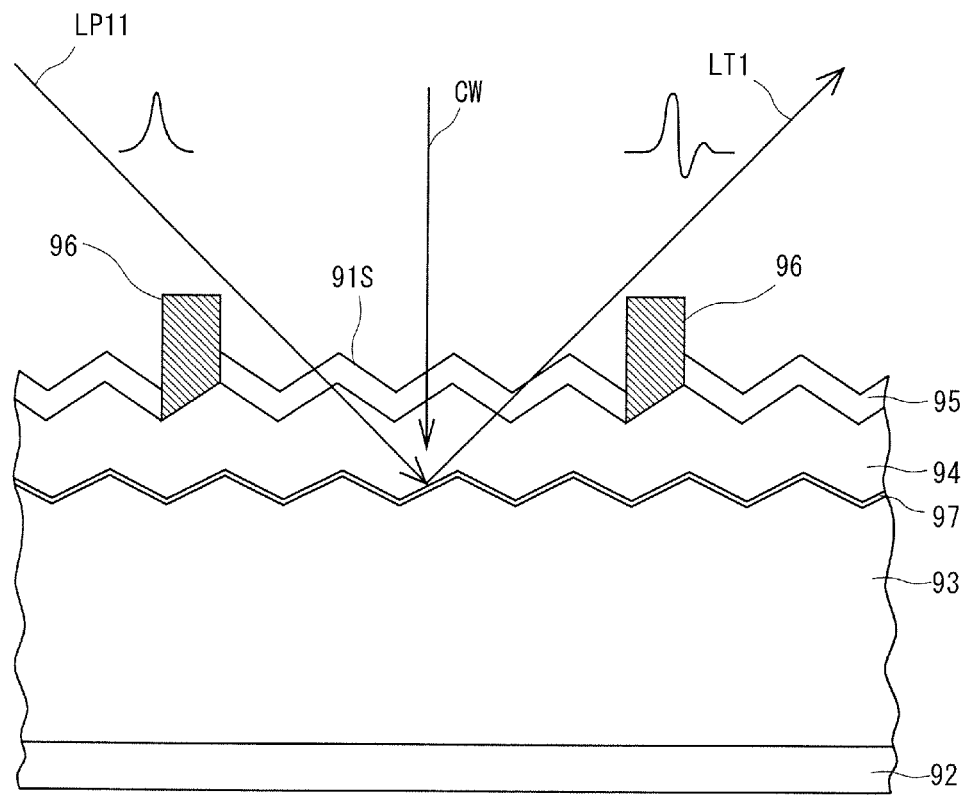
F I G. 3

F I G. 5
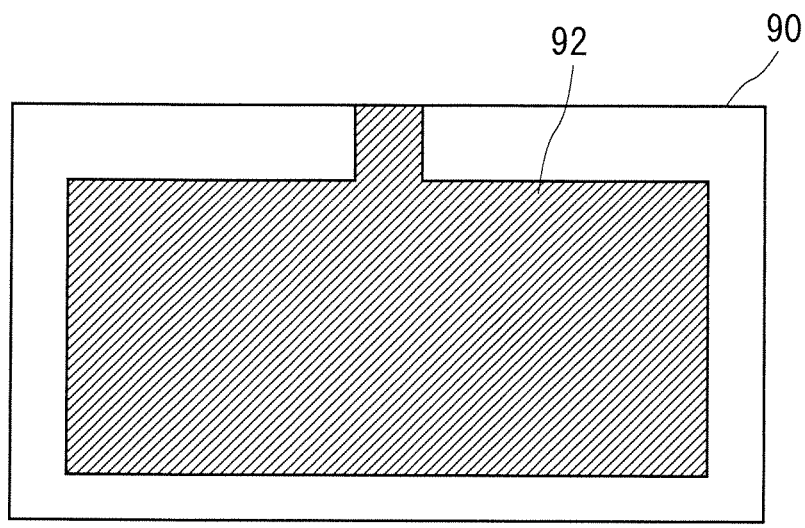

F I G. 8
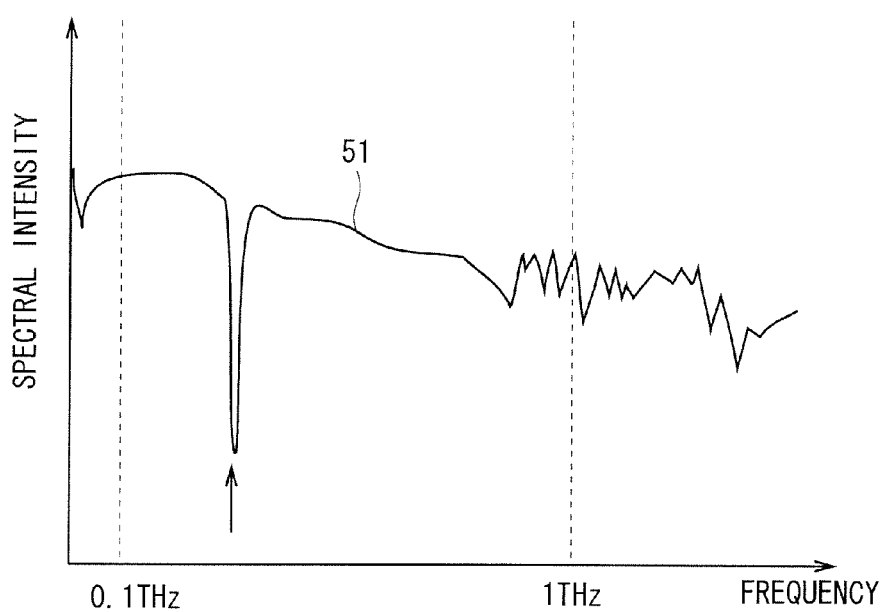

F I G. 9
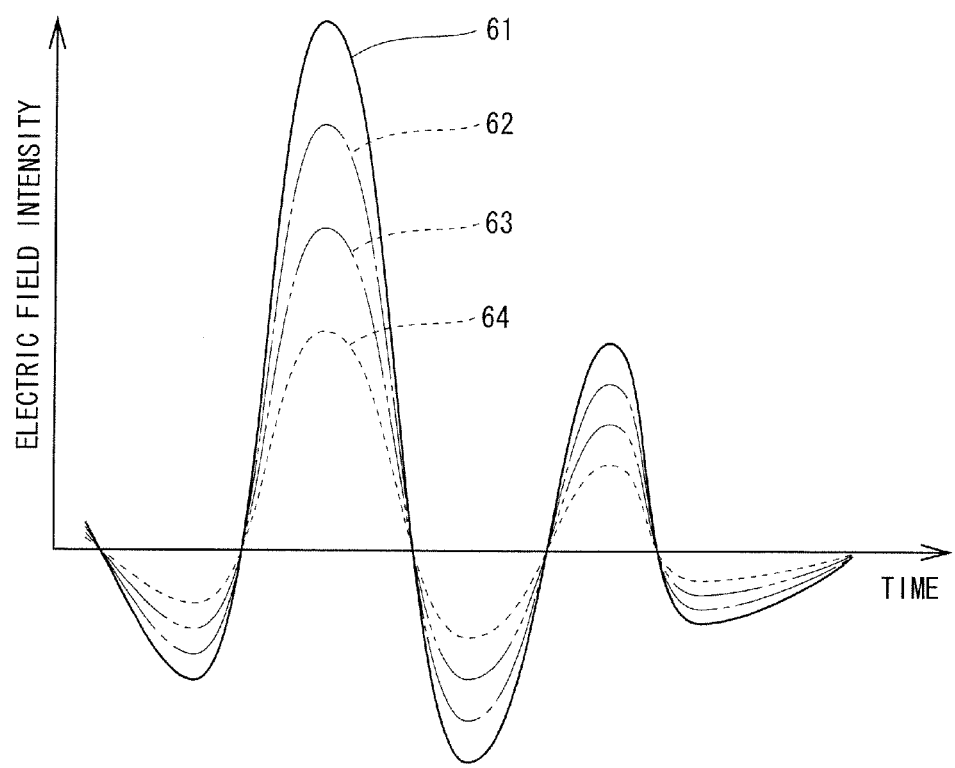

▨ : INTENSITIES OF 8 TO 10
▧ : INTENSITIES OF 4 TO 8
☐ : INTENSITIES OF 0 TO 4

INSPECTION APPARATUS AND INSPECTION METHOD

BACKGROUND OF THE INVENTION

1. Field of the Invention

The present invention relates to a technology of inspecting a photo device in a noncontact manner.

2. Description of the Background Art

An inspection apparatus that measures an electric characteristic of the photovoltaic cell by adopting what is called a four-terminal measurement method is used in a process of producing a photovoltaic cell that is of a kind of a photo device. Specifically, a current measuring probe pin and a voltage measuring probe pin are placed on collector electrodes provided in a light receiving surface and a rear surface of the photovoltaic cell. At this point, a voltage applied to the photovoltaic cell is changed while the photovoltaic cell is irradiated with pseudo-sunlight, thereby measuring a current-voltage relationship. Therefore, an I-V characteristic of the photovoltaic cell is measured (for example, see Japanese Patent Application Laid-Open No. 2010-182969).

SUMMARY OF THE INVENTION

In the conventional inspection apparatus for the photovoltaic cell, it is necessary to bring the current measuring probe pin or the voltage measuring probe pin into contact with the collector electrode. Therefore, there is a problem that the probe pin is worn down such that plating of the probe pin removes. Additionally, there is a risk of damaging a photovoltaic cell element during an inspection because the probe pin is brought into contact with the photovoltaic cell. Therefore, the inventors proposed a technique of inspecting the photo device in a noncontact manner (see Japanese Patent Application No. 2011-155665).

Specifically, in the case that the photo device is inspected in the noncontact manner, the photo device is irradiated with pulsed light emitted from a femtosecond laser, thereby generating a photoexcited carrier (a free electron and a hole). An electromagnetic wave (including a terahertz wave) is generated when the photoexcited carrier is accelerated by an internal electric field acting on a depletion layer of the photo device. That is, the electromagnetic wave can be generated according to a characteristic of a photoexcited carrier generation region by irradiating the photo device with the pulsed light. Accordingly, the characteristic (for example, a formation status of the depletion layer) of the photo device can be inspected by analyzing the generated electromagnetic wave.

However, the noncontact inspection of the photo device is performed without irradiating the photo device with the actual light (specifically, for example, artificial sunlight for the photovoltaic cell). Accordingly, it is difficult to detect a structural defect, which possibly becomes troublesome in use, and to evaluate performance of the photo device.

The present invention is directed to provide an inspection apparatus that inspects the photo device.

In accordance with one aspect of the present invention, an inspection apparatus that inspects a photo device includes: an irradiation part that irradiates the photo device with pulsed light emitted from a femtosecond laser; a detecting part that detects an electromagnetic wave, which is generated from the photo device according to the irradiation of the pump light; and a continuous light irradiation part that irradiates a portion, which is irradiated with the pump light in the photo device, with continuous light.

The irradiation of the continuous light can put the photo device into a state in which the electromotive force is generated. Therefore, the photo device in the usage state can be inspected. Accordingly, the detection of the structural defect, which possibly becomes troublesome in use, and the evaluation of the performance of the photo device can be performed in the noncontact manner by detecting the electromagnetic wave, which is generated according to the irradiation of the pulsed light.

Preferably the inspection apparatus further includes an irradiation condition changing part that changes an irradiation diameter or an intensity of the continuous light.

The range where the electromotive force is generated by the continuous light and magnitude of the generated electromotive force can arbitrarily be changed by changing the irradiation diameter or the intensity of the continuous light.

Preferably the continuous light includes pieces of light having plural wavelengths different from each other.

The photo device can be inspected while exposed to the pieces of continuous light having plural wavelengths different from each other.

Preferably the photo device is a photovoltaic cell, and the continuous light includes artificial sunlight.

The photovoltaic cell in the actually-used state can be inspected by irradiating the photovoltaic cell with the artificial sunlight.

Preferably the continuous light is a laser beam having a single wavelength.

The characteristic of the photo device depending on the wavelength can be inspected.

Preferably the inspection apparatus further includes a reverse bias voltage applying part that applies a voltage to put the photo device into a reverse bias state.

The internal electric field of the depletion layer is strengthened by putting the photo device into the reverse bias state, so that the intensity of the generated electromagnetic wave can be increased. Therefore, detection sensitivity of the electromagnetic wave can be improved.

The present invention is directed to provide an inspection method for inspecting the photo device.

In accordance with another aspect of the present invention, an inspection method for inspecting a photo device includes the steps of: (a) irradiating the photo device with pulsed light emitted from a femtosecond laser; (b) detecting an electromagnetic wave, which is generated from the photo device by the irradiation of the pulsed light; and (c) irradiating a portion, which is irradiated with the pulsed light in the photo device, with continuous light.

Therefore, an object of the present invention is to provide a technology of being able to perform the detection of the structural defect of the photo device, which possibly becomes troublesome in use, and the evaluation of the performance of the photo device in the noncontact manner These and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a schematic configuration diagram of an inspection apparatus according to a first preferred embodiment;

FIG. 3 is a schematic sectional view of a photovoltaic cell panel;

FIG. 5 is a plan view of a backside of a photovoltaic cell panel;

FIG. 8 is a view illustrating a spectral distribution of the electromagnetic wave pulse;

FIG. 9 is a view illustrating a time waveform of an electromagnetic wave pulse that is detected when intensity of continuous light is changed;

DESCRIPTION OF THE PREFERRED EMBODIMENTS

Hereinafter, preferred embodiments of the present invention will be described with reference to the accompanying drawings. Although the following preferred embodiments are examples in which the present invention is embodied, the technical scope of the present invention is not limited to the preferred embodiments.

1. First Preferred Embodiment

1.1. Configuration and Function

Figure 2:
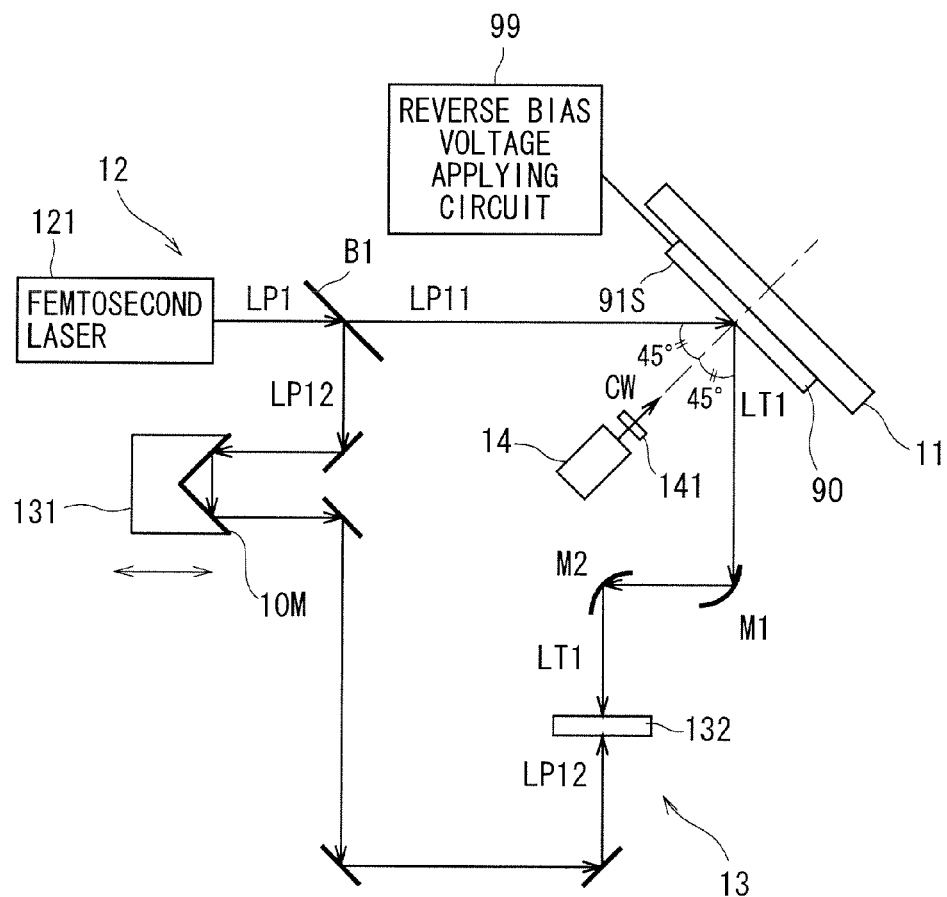
FIG. 2 is a schematic configuration diagram of an irradiation part and a detecting part according to the first preferred embodiment.

FIG. 1 is a schematic configuration diagram of an inspection apparatus 100 according to a first preferred embodiment. FIG. 2 is a schematic configuration diagram of an irradiation part 12 and a detecting part 13 according to the first preferred embodiment.

As illustrated in FIG. 1, the inspection apparatus 100 includes a stage 11, the irradiation part 12, the detecting part 13, a continuous light irradiation part 14, a motor 15, a control part 16, a monitor 17, and a manipulation inputting part 18. The inspection apparatus 100 is configured to inspect a photovoltaic cell panel 90 in which the photo device is formed.

When photo devices, such as a photovoltaic cell panel 90, are irradiated with pulsed light emitted from a femtosecond laser, an electromagnetic wave including a terahertz wave (frequencies of 0.1 to 30 THz) is generated from the photo devices. It is considered that the electromagnetic wave is generated based on the following principle. A photoexcited carrier is generated in the photo device by irradiating the photo device with the pulsed light having energy more than a bandgap. The generated photoexcited carrier is accelerated by internal electric fields (built-in electric fields), such as a depletion layer of the photo device and a metallic semiconductor interface, thereby generating a current. At this point, in the case that the irradiation light is the pulsed light, the time-variable pulsed current is generated, and therefore the electromagnetic wave is generated according to a Maxwell equation.

The electromagnetic wave generated from the photo device is radiated according to characteristics of photoexcited carrier generation regions, such as the depletion layer. Therefore, the characteristics of photoexcited carrier generation regions can be inspected by detecting the radiated electromagnetic wave. The inspection apparatus 100 is configured to detect the electromagnetic wave pulse, which is generated from the photovoltaic cell panel 90 according to the irradiation of the pulsed light having a predetermined wavelength, based on the principle.

An inspection target of the inspection apparatus 100 is not limited to the photovoltaic cell panel 90, but any sample may be used as an inspection target of the inspection apparatus 100 as long as the sample includes the photo device that converts visible light into the current. Examples of the photo device include image sensors such as a CMOS sensor and a CCD sensor in addition to the photovoltaic cell panel 90. In some of the image sensors, a light receiving element is formed in a portion that constitutes a rear surface side of the substrate, in which the photo device is formed, in a usage state. Even in such substrates, when a principal surface on a side on which the light is received in the usage state is placed as the light receiving surface on the inspection apparatus 100, the electromagnetic wave can well be detected.

The photovoltaic cell panel 90 is fixed on the stage 11 by fixing unit (not illustrated). Examples of fixing means includes a clipping tool that clips the photovoltaic cell panel 90, an adhesive sheet with which the photovoltaic cell panel 90 and the stage 11 adhere to each other, and a suction hole made in a surface of the stage 11. However, other fixing means may be used. In the first preferred embodiment, the stage 11 retains the photovoltaic cell panel 90 such that the irradiation part 12 and the detecting part 13 are disposed on a side of a light receiving surface 91S of the photovoltaic cell panel 90.

As illustrated in FIG. 2, the irradiation part 12 includes a femtosecond laser 121. The femtosecond laser 121 emits linearly-polarized pulsed light having wavelengths of 360 nm (nanometers) to 1 μm (micrometers), periods of several kilohertz to hundreds of megahertz, and pulse widths of 10 to 150 femtoseconds.

The pulsed light LP1 emitted from the femtosecond laser 121 is split into two by a beam splitter B1. The photovoltaic cell panel 90 is irradiated with one of the pieces of split pulsed light (hereinafter referred to as pump light LP11). At this point, the irradiation part 12 performs the irradiation of the pump light LP11 from the side of the light receiving surface 91S. The photovoltaic cell panel 90 is irradiated with the pump light LP11 such that an optical axis of the pump light LP11 is obliquely incident to the light receiving surface 91S of the photovoltaic cell panel 90. In the example in FIG. 2, an incident angle of the pump light LP11 is set to 45 degrees. However, the incident angle may properly be changed in a range of 0 degree to 90 degrees.

Figure 4:
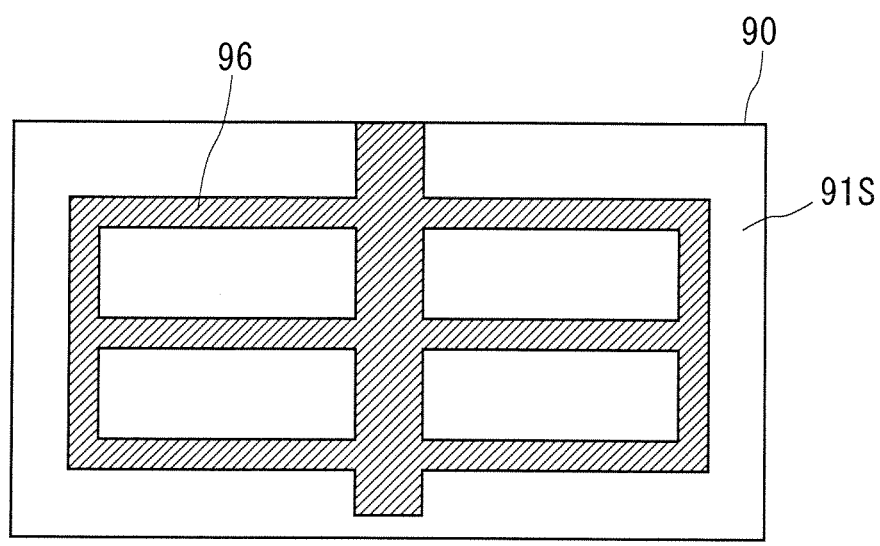
FIG. 4 is a plan view of the photovoltaic cell panel when viewed from a light receiving surface side.

FIG. 3 is a schematic sectional view of the photovoltaic cell panel 90. FIG. 4 is a plan view of the photovoltaic cell panel 90 when viewed from the light receiving surface side 91S. FIG. 5 is a plan view of a backside of the photovoltaic cell panel 90. As illustrated in FIG. 3, the photovoltaic cell panel 90 has a stacked structure, in which a planar rear surface electrode 92 made of aluminum, a p-type silicon layer 93, an n-type silicon layer 94, an antireflection film 95, and a lattice-shaped aluminum light receiving surface electrode 96 are sequentially stacked from a bottom.

A portion in which the p-type silicon layer 93 and the n-type silicon layer 94 are coupled constitutes a pn junction 97 in which the depletion layer is formed. When the portion is irradiated with the pulsed light, the generated photoexcited carrier is accelerated by the internal electric field, thereby generating the electromagnetic wave. The generated electromagnetic wave is externally radiated, and therefore the electromagnetic wave is observed as electromagnetic wave pulse LT1 by a detector 132.

The photovoltaic cell panel 90 may be made of a material (for example, amorphous silicon) except a crystalline silicon. Generally, the bandgap (for example, 1.75 eV to 1.8 eV) of the amorphous silicon photovoltaic cell is larger than the bandgap (for example, 1.2 eV) of the crystalline silicon photovoltaic cell. Accordingly, for the amorphous silicon photovoltaic cell, for example, the electromagnetic wave including the terahertz wave can well be generated from the amorphous silicon photovoltaic cell by setting the wavelength of the pulsed light emitted from the femtosecond laser 121 to 700 µm or less. In other semiconductor photovoltaic cells, the electromagnetic wave including the terahertz wave can well be generated based on the similar principle.

The antireflection film 95 is made of silicon oxide, silicon nitride, or titanium oxide. In the photovoltaic cell panel 90, the principal surfaces on the side on which the light receiving surface electrode 96 is provided constitutes the light receiving surface 91S in the principal surfaces in which collector electrodes (the light receiving surface electrode 96 or the rear surface electrode 92) are provided. That is, the photovoltaic cell panel 90 is designed to generate an electric power by receiving the light from the side of the light receiving surface 91S. The light receiving surface electrode 96 may be not the aluminum electrode but a transparent electrode in order to improve a daylighting property.

The light receiving surface 91S of the photovoltaic cell panel 90 has a necessary texture structure in order to suppress a reflection loss of the light. Specifically, irregularities of several micrometers to tens micrometers is formed by anisotropic etching, or a V-shape groove is formed by a mechanical method. Thus, the light receiving surface 91S of the photovoltaic cell panel 90 is generally formed such that lighting can efficiently be performed as much as possible. Accordingly, the light with which the photovoltaic cell panel 90 is irradiated easily reaches the pn junction 97. For the photovoltaic cell panel 90, the light can easily reach the pn junction 97 when the light has wavelengths of 1 µm or less, which are of the wavelength domain of the visible light.

Referring to FIG. 2, the other piece of pulsed light split by the beam splitter B1 is incident as probe light LP12 to the detector 132 through a delaying part 131 and a mirror. The electromagnetic wave, which is generated according to the irradiation of the pulsed light LP11 that is of the pulsed light, is collected by paraboloid mirrors M1 and M2 and incident to the detector 132.

The detector 132 is constructed by a photoconductive switch. When the detector 132 is irradiated with the probe light LP12 while the electromagnetic wave generated from the photovoltaic cell panel 90 is incident to the detector 132, a current is instantaneously generated in the detector 132 according to electric field intensity of the electromagnetic wave pulse. The current corresponding to the electric field intensity is converted into a digital amount through an I/V conversion circuit and an A/D conversion circuit. Therefore, the detecting part 13 detects the electric field intensity of the electromagnetic wave pulse generated from the photovoltaic cell panel 90 according to the irradiation of the probe light LP12. In the first preferred embodiment, the photoconductive switch is used as the detector 132. Alternatively, another element such as a nonlinear optical crystal may be used as the detector 132. The electromagnetic wave may be detected using a Schottky barrier diode instead of the photoconductive switch.

The delaying part 131 is an optical element that continuously changes a time necessary for the probe light LP12 to reach the detector 132 from the beam splitter B1. The delaying part 131 is fixed to a moving stage (not illustrated) that moves in an incident direction of the probe light LP12. The delaying part 131 includes a folding mirror 10M that folds the probe light LP12 in the incident direction. Under the control of the control part 16, the delaying part 131 drives the moving stage to move a folding mirror 10M, thereby precisely changing an optical path length of the probe light LP12. Therefore, the delaying part 131 changes a temporal difference between a time necessary for the electromagnetic wave pulse to reach the detecting part 13 and a time necessary for the probe light LP12 to reach the detecting part 13. When the delaying part 131 changes an optical distance (the optical path length) of an optical path (a second optical path) of the probe light LP12, timing (detection timing or sampling timing), in which the electric field intensity of the electromagnetic wave pulse LT1 is detected, can be accelerated or delayed in the detecting part 13 (the detector 132).

The temporal difference between the time necessary for the electromagnetic wave pulse LT1 to reach the detecting part 13 and the time necessary for the probe light LP12 to reach the detecting part 13 may be changed by another mode. A length of an optical path (a first optical path) of the pump light LP11 may be changed. In this case, the time necessary for the electromagnetic wave pulse LT1 to reach the detector 132 and the time necessary for the probe light LP12 to reach the detector 132 can relatively be deviated. Accordingly, the detection timing of the electric field intensity of the electromagnetic wave pulse LT1 can be delayed in the detector 132. An electrooptic effect may be used. That is, an electrooptic element, in which a refractive index is changed by changing an applied voltage, may be used as the delay element. Specifically, an electrooptic element disclosed in Japanese Patent Application Laid-Open No. 2009-175127 can be used.

As illustrated in FIG. 2, a reverse bias voltage applying circuit 99 (a reverse bias voltage applying part) that applies a reverse bias voltage between the rear surface electrode 92 and the light receiving surface electrode 96 during the inspection is connected to the photovoltaic cell panel 90. When the reverse bias voltage is applied between the electrodes, the depletion layer formed in the pn junction 97 is enlarged to increase the internal electric field. Therefore, mobility of the photoexcited carrier generated according to the irradiation of the pump light LP11 can be enhanced. Accordingly, the electric field intensity of the electromagnetic wave pulse LT1 detected by the detector 132 is increased, so that detection sensitivity of the electromagnetic wave pulse LT1 can be improved in the detecting part 13. However, the reverse bias voltage applying circuit 99 may be eliminated.

The continuous light irradiation part 14 irradiates the photovoltaic cell panel 90 with continuous light CW. The kind of the continuous light CW output from the continuous light irradiation part 14 is properly selected depending on the inspection use. There is no particular limitation to the continuous light CW. Specifically, the continuous light CW is the light including plural wavelengths, such as the sunlight, the artificial sunlight that represents the sunlight, light having relatively wide wavelength distribution like an incandescent lamp, and light having wavelengths (for example, 400 nm, 600 nm, and 800 nm) corresponding to RGB three primary colors like an LED lamp and a fluorescent lamp. For example, the continuous light CW may be the light having the single wavelength, which is selected from a range of an ultraviolet ray to a near-infrared ray.

The continuous light irradiation part 14 is constructed according to the wavelength of the light used in the inspection. Specifically, for example, the continuous light irradiation part 14 is constructed by a semiconductor laser, an LED, a halogen lamp, a xenon lamp, and a combination thereof. A wavelength-variable laser may be used as the continuous light irradiation part 14. For example, a distributed feedback type (DFB) laser, in which the wavelength of the emitted laser beam can substantially continuously be change (for example, in each 2 nm) by temperature control, can be used as the wavelength-variable laser.

In the inspection apparatus 100, the irradiation position of the pump light LP11 is irradiated with the continuous light CW, which allows the electromagnetic wave pulse LT1 to be generated while the photovoltaic cell panel 90 is irradiated with the continuous light CW (that is, while the electromotive force is generated). For example, in the case that the photovoltaic cell panel 90 is irradiated with the artificial sunlight, the state in which the photovoltaic cell panel 90 is exposed to the sunlight outside the room can be reproduced. The detection of the structural defect, which possibly becomes troublesome in use of the photovoltaic cell panel 90, and the evaluation of the performance of the photovoltaic cell panel 90 can be performed by analyzing the generated electromagnetic wave pulse LT1. The characteristic of the photovoltaic cell panel 90 depending on the wavelength can be inspected by irradiating the photovoltaic cell panel 90 with the continuous light CW having the specific wavelength.

The continuous light irradiation part 14 includes an irradiation condition changing part 141. The irradiation condition changing part 141 changes the spot diameter of the continuous light CW with which the photovoltaic cell panel 90 is simultaneously irradiated. The range where the electromotive force is generated can arbitrarily be changed by changing the range, where the photovoltaic cell panel 90 is irradiated at one time with the continuous light CW, using the irradiation condition changing part 141.

For example, when a beam diameter (the irradiation diameter) of the continuous light CW is set to 50 μm or more while a beam diameter (the irradiation diameter) of the pump light LP11 is set to 50 μm, the electromotive force is also generated in a surrounding portion of the region irradiated with the pump light LP11. At this point, the photoexcited carrier generated by the irradiation of the pump light LP11 has a high possibility that the photoexcited carrier is affected by the surrounding portion. Accordingly, desirably the surrounding portion is irradiated with the continuous light CW in order to inspect the photovoltaic cell panel 90 in usage state. The continuous light CW is not necessarily formed into the locally spot shape. For example, the whole photovoltaic cell panel 90 may simultaneously be irradiated with the continuous light CW.

The irradiation condition changing part 141 changes the light intensity of the continuous light CW. The magnitude of the generated electromotive force can arbitrarily be changed by changing the light intensity of the continuous light CW with which the photovoltaic cell panel 90 is irradiated. Therefore, the inspection of the photovoltaic cell panel 90 can be performed according to a power generation state. For example, use of a light blocking filter is considered as means for changing the intensity of the continuous light CW. However, there is no particular limitation to the means for changing the intensity of the continuous light CW. Obviously the light intensity of the continuous light CW output from the continuous light irradiation part 14 may directly be changed.

The motor 15 drives an X-Y table (not illustrated) that moves the stage in a two-dimensional plane. The motor 15 drives the X-Y table to relatively move the photovoltaic cell panel 90 retained by the stage 11 with respect to the irradiation part 12. The inspection apparatus 100 can move the photovoltaic cell panel 90 to an arbitrary position in the two-dimensional plane using the motor 15. The inspection apparatus 100 can irradiate the wide range of the photovoltaic cell panel 90 with the continuous light CW and the pump light LP11 using the motor 15. Alternatively, means for moving the irradiation part 12 and the continuous light irradiation part 14 in the two-dimensional plane may be provided instead of the movement of the photovoltaic cell panel 90, or the means may be provided while the photovoltaic cell panel 90 is moved. An operator may manually move the stage 11.

The control part 16 includes a configuration as a general computer (not illustrated) that includes a CPU, a ROM, a RAM, and an auxiliary storing part (for example, a hard disk). The control part 16 is connected to the irradiation part 12, the detecting part 13, the continuous light irradiation part 14, and the motor 15 to control operations of these parts. Specifically, the control part 16 receives data related to the electric field intensity of the electromagnetic wave pulse LT1 from the detector 132. The control part 16 controls the movement of the moving stage (not illustrated) that moves the delaying part 131, and receives data related to the position of the delaying part 131, such as a moving distance of the folding mirror 10M, from a linear scale provided in the moving stage.

The control part 16 is connected to a time waveform constructing part 21, a spectrum analyzing part 23, and an image generating part 25, and the control part 16 causes each part to perform various pieces of calculation processing. The time waveform constructing part 21, the spectrum analyzing part 23, and the image generating part 25 may be constructed in a software manner such that a CPU (not illustrated) is operated according to a program, or part or the whole of the functions may be constructed in a hardware manner by a dedicated circuit.

Based on the electric field intensity detected by the detecting part 13 (the detector 132), the time waveform constructing part 21 constructs a time waveform of the electromagnetic wave pulse LT1 with respect to the electromagnetic wave pulse LT1 generated in the photovoltaic cell panel 90. Specifically, the electric field intensity of the electromagnetic wave pulse LT1 is detected by plural pieces of detection timing different from each other by moving the delaying part 131, thereby reconstructing the time waveform. The reconstruction method is described later.

The spectrum analyzing part 23 performs a spectral analysis based on the time waveform of the electromagnetic wave pulse LT1. Specifically, the spectrum analyzing part 23 acquires an amplitude intensity spectrum for the frequency by performing a Fourier transformation to the time waveform of the electromagnetic wave pulse LT1.

The image generation part 25 generates an image, in which a distribution of the electric field intensity of the generated electromagnetic wave pulse LT1 is visualized, with respect to an inspection target area (part or a whole of the photovoltaic cell panel 90) on the photovoltaic cell panel 90. Specifically, for the image expressing the light receiving surface 91S of the photovoltaic cell panel 90, a portion corresponding to each measurement point is painted in each color according to the electric field intensity of the actually-measured electromagnetic wave pulse LT1. Therefore, the electric field intensity distribution image is generated.

As illustrated in FIG. 1, the monitor 17 and the manipulation inputting part 18 are connected to the control part 16. The monitor 17 is display devices, such as a liquid crystal display, and displays various pieces of image information to the operator. For example, the image of the light receiving surface 91S of the photovoltaic cell panel 90, in which the picture is taken by a camera, and the electric field intensity distribution image generated by the image generation part 25 are displayed on the monitor 17. A GUI screen used to set inspection conditions (for example, an inspection region in the photovoltaic cell panel 90 and irradiation intensity or irradiation range of the continuous light CW) may be displayed on the monitor 17.

1.2. Inspection of Photo Device

An inspection flow of the photovoltaic cell panel 90 that is of the photo device will be described below. The inspection apparatus 100 of the first preferred embodiment is configured to be able to perform two kinds of inspections (a first inspection and a second inspection).

The first inspection is performed based on the time waveform of the electromagnetic wave pulse LT1. In the first inspection, a specific position (an interest position) to be inspected on the photovoltaic cell panel 90 is irradiated with the continuous light CW and the pump light LP11 that is of the pulsed light. The time waveform of the electromagnetic wave pulse LT1, which is generated according to the irradiation of the pump light LP11, is reconstructed. A spectral analysis is performed to the reconstructed time waveform.

The second inspection is performed based on an electric field intensity distribution of the electromagnetic wave pulse LT1, which is generated according to the irradiation of the pump light LP11. In the second inspection, each point on the photovoltaic cell panel 90 is irradiated with the continuous light CW and the pump light LP11. The electric field intensities of the electromagnetic wave pulses LT1 generated at the points are calculated. Hereinafter, the first inspection is first described, and then the second inspection is described. In the following description, unless otherwise noted, it is assumed that each operation of the inspection apparatus 100 is controlled by the control part 16.

First Inspection

Figure 6:
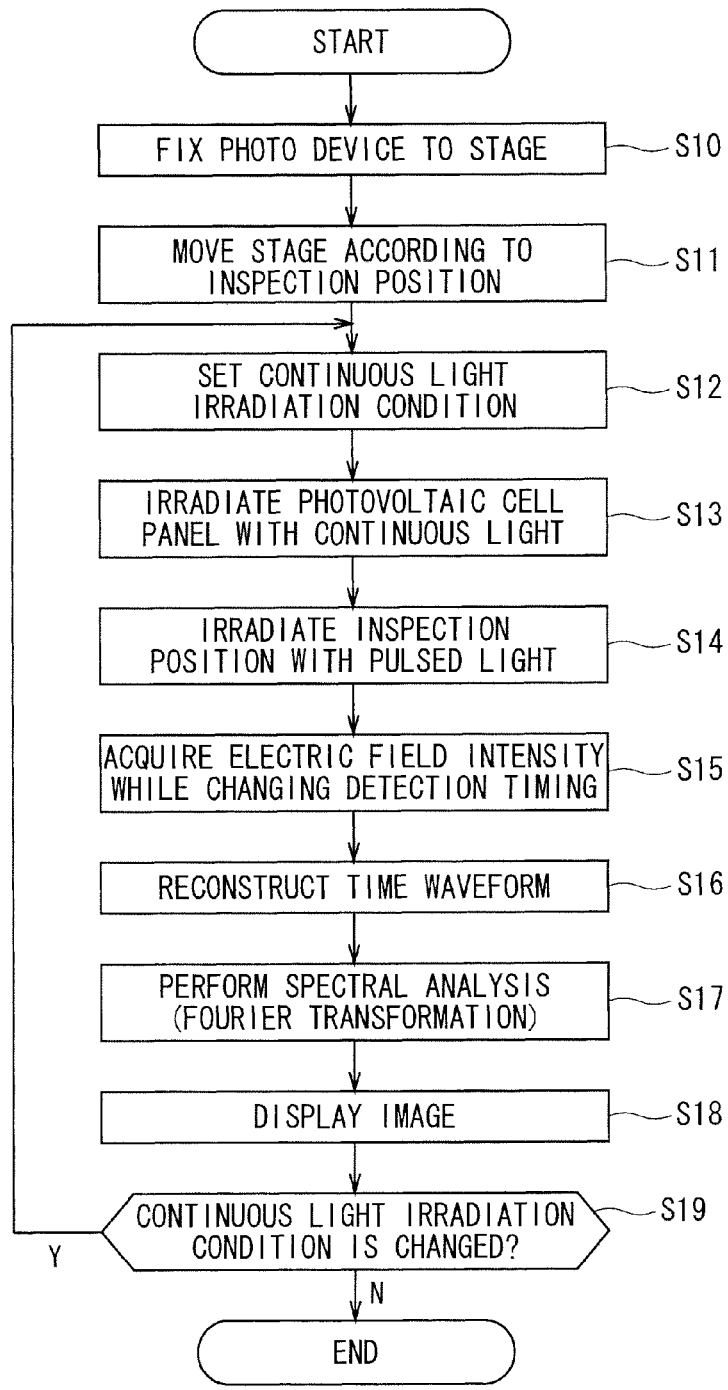
FIG. 6 is a flowchart of a first inspection.

FIG. 6 is a flowchart of the first inspection. The flow of the first inspection is illustrated in FIG. 6 by way of example. Accordingly, some processes may concurrently be performed, or the sequence to perform some processes may properly be changed.

The photovoltaic cell panel 90 that constitutes the inspection target is fixed to the stage 11 (Step S10). The operator may carry the photovoltaic cell panel 90 to the stage 11, or a conveying device (not illustrated) may carry the photovoltaic cell panel 90 to the stage 11. At this point, as described above, the photovoltaic cell panel 90 is placed such that the light receiving surface 91S of the photovoltaic cell panel 90 is irradiated with the pulsed light LP11.

When the photovoltaic cell panel 90 is fixed to the stage 11, the inspection apparatus 100 moves the photovoltaic cell panel 90 according to the interest position (Step S11). Using the manipulation inputting part 18, the operator previously inputs the interest position as data (coordinate data) related to the position on the photovoltaic cell panel 90 to be inspected. In order to irradiate the interest position with the pulsed light LP11, the control part 16 drives the motor 15 to move the stage 11 based on the coordinate data. The operator may manually move the stage 11 to move the photovoltaic cell panel 90 according to the interest position.

The irradiation conditions of the continuous light CW are set (Step S12). Specifically, for example, the irradiation range of the continuous light CW and the intensity of the continuous light CW are set. In the case that the continuous light irradiation part 14 is configured to be able to irradiate the photovoltaic cell panel 90 with pieces of continuous light CW having different wavelengths, the wavelengths of the pieces of continuous light CW output in Step S12 are set. The irradiation condition changing part 141 properly changes the light blocking region such that the irradiation diameter of the continuous light CW becomes the setting value. The continuous light irradiation part 14 starts the irradiation of the continuous light CW based on the set irradiation condition of the continuous light CW (Step S13).

The inspection apparatus 100 irradiates the inspection position of the photovoltaic cell panel 90 with the pump light LP11 (Step S14). The inspection apparatus 100 detects the electric field intensity of the electromagnetic wave pulse LT1 generated by the irradiation of the pulsed light LP11 (Step S15). In Step S15, when the electric field intensity of the electromagnetic wave pulse LT1 is detected, the control part 16 controls the delaying part 131 to delay the timing at which the probe light LP12 reaches the detector 132. Therefore, the electric field intensity of the electromagnetic wave pulse LT1 is detected at plural pieces of detection timing different from each other. In irradiating the photovoltaic cell panel 90 with the pump light LP11, the reverse bias voltage may be applied between the electrodes of the photovoltaic cell panel 90 by driving the reverse bias voltage applying circuit 99.

The inspection apparatus 100 reconstructs the time waveform of the electromagnetic wave pulse LT1 based on the detection result of the electric field intensity acquired in Step S15 (Step S16). Specifically, the time waveform constructing part 21 reconstructs the time waveform of the electromagnetic wave pulse LT1 by plotting a value of the electric field intensity detected in Step S15 along a temporal axis.

Figure 7:
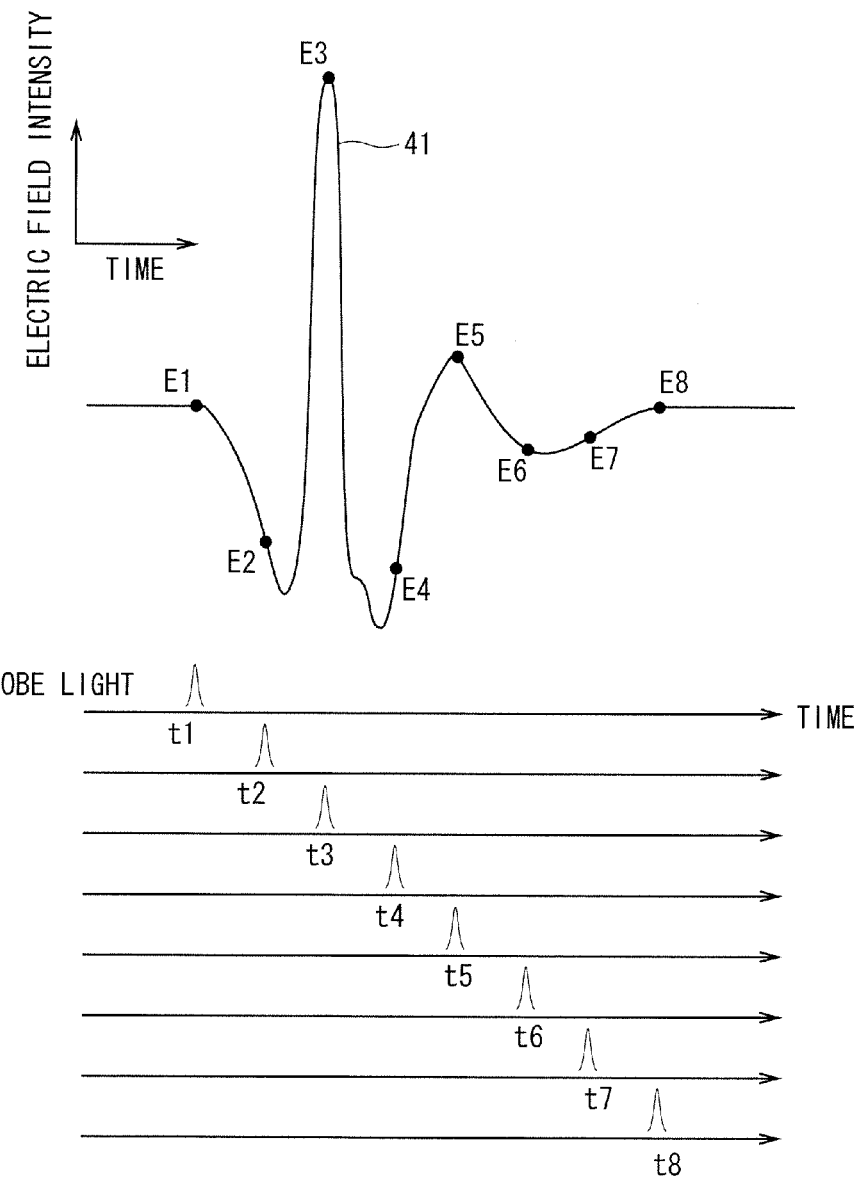
FIG. 7 is a view illustrating a time waveform of an electromagnetic wave pulse reconstructed by a time waveform constructing part.

FIG. 7 is a view illustrating the time waveform of the electromagnetic wave pulse LT1 reconstructed by the time waveform constructing part 21. In FIG. 7, a horizontal axis indicates the time, and a vertical axis indicates the electric field intensity. A lower stage of FIG. 7 conceptually illustrates plural pieces of probe light LP12 in which the timing (that is, pieces of detection timing t1 to t8), at which the probe light LP12 reaches the detector 132, is varied by the delaying part 131.

When the interest position is irradiated with the pump light LP11, the electromagnetic wave pulse LT1 having a time waveform 41 in FIG. 7 repeatedly comes in the detector 132 in a predetermined period. At this point, for example, when the delaying part 131 is adjusted such that the probe light LP11 reaches the detector 132 at the detection timing t1, the detector 132 detects the electric field intensity of a value E1. In the case that the delaying part 131 is adjusted such that the detection timing becomes t2 to t8, the electric field intensities having values E2 to E8 corresponding to the pieces of detection timing t2 to t8 are detected. The time waveform 41 of the electromagnetic wave pulse LT1 is reconstructed by plotting the acquired electric field intensity values E1 to E8 on the graph along the temporal axis.

The characteristic of the photoexcited carrier generation region can be inspected at the interest position by reconstructing the time waveform 41. For example, a formation defect of the photoexcited carrier generation region can be detected by the existence or non-existence of the detection of the electromagnetic wave pulse LT1 or an amplitude of the electric field intensity of the reconstructed electromagnetic wave pulse LT1. Particularly, in the first preferred embodiment, the irradiation of the continuous light CW can put the photovoltaic cell panel 90 into the usage state (that is, the state in which the electromotive force is generated). The electromagnetic wave pulse LT1 generated under the above situation corresponds to the characteristic of the photoexcited carrier generation region when the photovoltaic cell panel 90 is in the usage state. Accordingly, the defect that possibly becomes troublesome in use of the photovoltaic cell panel 90 can be detected, or the performance of the photovoltaic cell panel 90 can be evaluated.

Referring to FIG. 6, when a time waveform 41 of the electromagnetic wave pulse LT1 is reconstructed, the inspection apparatus 100 performs the spectral analysis (Step S17). Specifically, the spectrum analyzing part 23 performs the Fourier transformation based on the time waveform acquired in Step S16. Therefore, a spectral distribution of the electromagnetic wave pulse LT1 is acquired. The spectral analysis in Step S17 may be eliminated.

FIG. 8 is a view illustrating a spectral distribution 51 of the electromagnetic wave pulse LT1. In FIG. 8, a vertical axis indicates a spectral intensity and a horizontal axis indicates a frequency. As illustrated in the spectral distribution 51, the electromagnetic wave pulse LT1 generated from the photovoltaic cell panel 90 has the relatively strong spectral intensity at frequencies of 0.1 THz to 1 THz.

Various pieces of information on a physical properties can be obtained with respect to the interest position in the photovoltaic cell panel 90 by acquiring the spectral distribution 51. For example, the information on the physical property can relatively be evaluated at the interest position of the photovoltaic cell panel 90 by comparing the spectral distribution 51 in FIG. 8 to a reference spectral distribution. In the spectral distribution 51, as indicated by an arrow, absorption is generated with respect to the electromagnetic wave having a specific frequency. That an impurity absorbing the specific frequency is formed at the interest position is deduced from the absorption of the spectral distribution 51, and a kind or a concentration of the impurity is also deduced from the frequency of the absorbed electromagnetic wave.

Referring to FIG. 6, when the spectral analysis is completed, the image indicating the inspection result is displayed on the monitor 17 (Step S18). Specifically, for example, the time waveform (see FIG. 7) of the electromagnetic wave pulse LT1 acquired in Step S16 and the spectral distribution (see FIG. 8) acquired in Step S17 are displayed as the analysis result on the monitor 17.

The inspection apparatus 100 determines whether the irradiation condition of the continuous light CW is changed to perform the additional inspection (Step S19). When the additional inspection is performed (YES in Step S19), the inspection apparatus 100 returns to Step S12 to set the irradiation condition of the continuous light CW. When the additional inspection is not performed (NO in Step S19), the inspection apparatus 100 ends the operation related to the first inspection.

FIG. 9 is a view illustrating time waveforms 61 to 64 of the electromagnetic wave pulse LT1 that is detected when the intensity of the continuous light CW is changed. A time waveform 61 corresponds to the electromagnetic wave pulse LT1 that is detected when the photovoltaic cell panel 90 is not irradiated with the continuous light CW, and time waveforms 62 to 64 correspond to the electromagnetic wave pulses LT1 in which the intensities of the continuous light CW are sequentially increased.

As illustrated in FIG. 9, the amplitude of the electromagnetic wave pulse LT1 is relatively decreased by the irradiation of the continuous light CW. This is attributed to the following fact. That is, when the photovoltaic cell panel 90 is irradiated with the continuous light CW, a conduction band is filled with the photoexcited carriers excited by the continuous light CW. Therefore, it is considered that a change in current of the photoexcited carrier generated by the pump light LP11 is relatively weakened, and that the electric field intensity of the generated electromagnetic wave pulse LT1 is also weakened.

At the inspection points where the time waveforms 61 to 64 are detected, the amplitude of the electromagnetic wave pulse LT1 is decreased with increasing electric field intensity of the continuous light CW. However, a tendency of the change in amplitude of the electromagnetic wave pulse LT1 corresponding to the intensity of the continuous light CW is not necessarily common to all the points of the photovoltaic cell panel 90. That is, sometimes the tendency may vary according to the formation situation of the depletion layer.

Second Inspection

Figure 10:
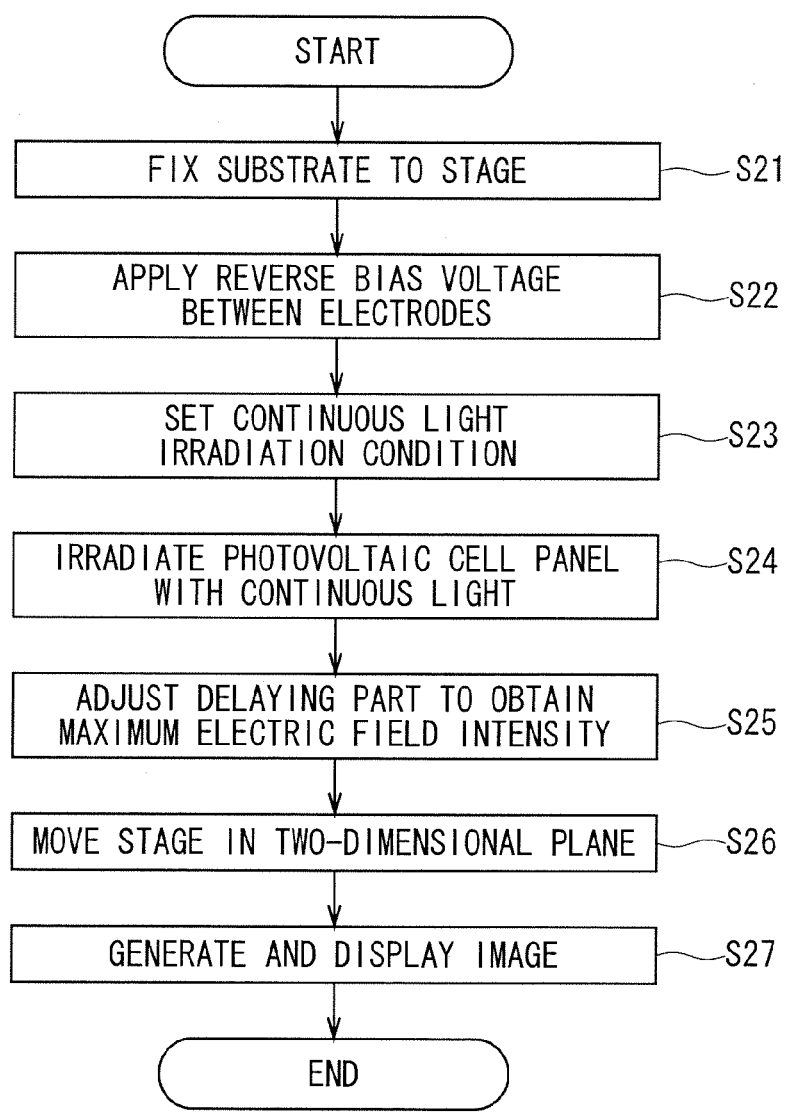
FIG. 10 is a flowchart of a second inspection.

Then the second inspection will be described. FIG. 10 is a flowchart of the second inspection. In the second inspection, the photovoltaic cell panel 90 is fixed to the stage 11 (Step S21). The process in Step S21 is identical to that in Step S11 of the first inspection in FIG. 6. The reverse bias voltage is applied between the rear surface electrode 92 and the light receiving surface electrode 96 of the photovoltaic cell panel 90 (Step S22). It is not always necessary to apply the reverse bias voltage, but the second inspection may be performed with no reverse bias voltage.

The irradiation conditions of the continuous light CW are set (Step S23). The irradiation of the continuous light CW is started based on the irradiation condition set in Step S23 (Step S24). Steps S23 and S24 are substantially identical to Steps S12 and S13 of the first inspection in FIG. 6.

The inspection apparatus 100 irradiates the photovoltaic cell panel 90 with the continuous light CW, and irradiates the photovoltaic cell panel 90 with the pump light LP11 to generate the electromagnetic wave pulse LT1. There is no particular limitation to the position where the photovoltaic cell panel 90 is irradiated with the continuous light CW and the position where the photovoltaic cell panel 90 is irradiated with the pump light LP11, and the continuous light CW and the pump light LP11 are set to the position where the electromagnetic wave pulse LT1 enough to detect the electric field intensity is generated. In the inspection apparatus 100, the delaying part 131 is adjusted such that the electric field intensity of the electromagnetic wave pulse LT1 detected by the detector 132 is maximized (Step S25). Specifically, the position of the folding mirror 10M is adjusted in the delaying part 131 to change the timing at which the probe light LP12 reaches the detector 132.

For example, for the electromagnetic wave pulse LT1 having the time waveform 41 in FIG. 7, when the electromagnetic wave pulse LT1 is detected at the detection timing t3, the maximum intensity of the electromagnetic wave pulse LT1 can be detected by the detector 132. Accordingly, in this case, the inspection apparatus 100 moves the folding mirror 10M to the position corresponding to the detection timing t3.

Thus, the electromagnetic wave pulse LT1 is easily detected by detecting the maximum intensity of the electromagnetic wave pulse LT1. Therefore, the detection sensitivity of the electromagnetic wave pulse LT1 can be improved, and the photovoltaic cell panel 90 can properly be inspected. It is not always necessary that the detector 132 detect the maximum intensity of the electromagnetic wave pulse LT1. That is, the detection timing can arbitrarily be set as long as the detector 132 can perform the measurement.

In setting the detection timing in Step S25, it is not always necessary to irradiate the photovoltaic cell panel 90 with the continuous light CW. Therefore, the continuous light irradiation part 14 can interrupt the irradiation of the photovoltaic cell panel 90 with the continuous light CW while the process in Step S25 is performed.

When the adjustment of the delaying part 131 is completed, the inspection apparatus 100 drives the motor 15 to move the photovoltaic cell panel 90 in the two-dimensional plane (Step S26). At this point, the photovoltaic cell panel 90 is irradiated with the continuous light CW and the pump light LP11. The detector 132 detects the electric field intensity of the electromagnetic wave pulse LT1, which is generated according to the irradiation of the pump light LP11. Therefore, the electric field intensities of the electromagnetic wave pulses LT1 generated from the points in the inspection target region on the photovoltaic cell panel 90 are acquired.

Figure 11:
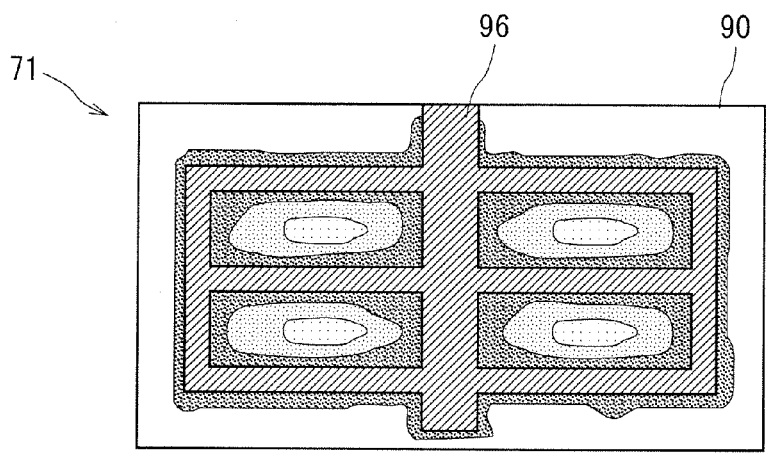
FIG. 11 is a view illustrating an example of an electric field intensity distribution image.

Based on the acquired electric field intensities, the inspection apparatus 100 generates the image indicating the electric field intensity distribution, and displays the image on the monitor 17 (Step S27). FIG. 11 is a view illustrating an example of an electric field intensity distribution image 71. In the electric field intensity distribution image 71, according to the magnitude of the electric field intensity of the electromagnetic wave pulse LT1, corresponding portions of the image expressing the photovoltaic cell panel 90 are painted in plural colors. In FIG. 11, the difference of the color is expressed by the difference of hatching. In the electric field intensity distribution image 71, the magnitude of the electric field intensity is classified into three stages (intensities of 0 to 4, intensities of 4 to 8, and intensities of 8 to 10), and the stages are painted in colors according to the classification. Alternatively, the magnitude of the electric field intensity is classified into two stages or at least four stages, and the stages may be painted in colors.

As illustrated in FIG. 11, in the electric field intensity distribution image 71, the relatively strong electromagnetic wave pulse LT1 is detected in the surrounding portion of the light receiving surface electrode 96, and the detected electric field intensity is weakened with distance from the light receiving surface electrode 96. This is attributed to the fact that, because the relatively strong internal electric field acts on the portion close to the electrode, such as the light receiving surface electrode 96, the electric field intensity of the generated electromagnetic wave pulse LT1 is relatively strengthened.

A formation status of the photoexcited carrier generation area can widely be recognized at once with respect to the photovoltaic cell panel 90 by generating the electric field intensity distribution image 71. Particularly, in the first preferred embodiment, the photovoltaic cell panel 90 is also irradiated with the continuous light CW, so that the detection of the structural defect, which possibly becomes troublesome in use, and the evaluation of the performance of each portion in the photovoltaic cell panel 90 can efficiently be performed.

In the second inspection, only the instantaneous electric field intensity is detected in the electromagnetic wave pulse LT1. Alternatively, as described in the first inspection, the time waveform of the electromagnetic wave pulse LT1 may be reconstructed at each point by controlling the delaying part 131. For example, the image in which a spectral intensity of a specific frequency is expressed by color shading may be formed based on the spectral distribution, which is obtained by performing the Fourier transformation of the acquired time waveform.

2. Second Preferred Embodiment

Figure 12:
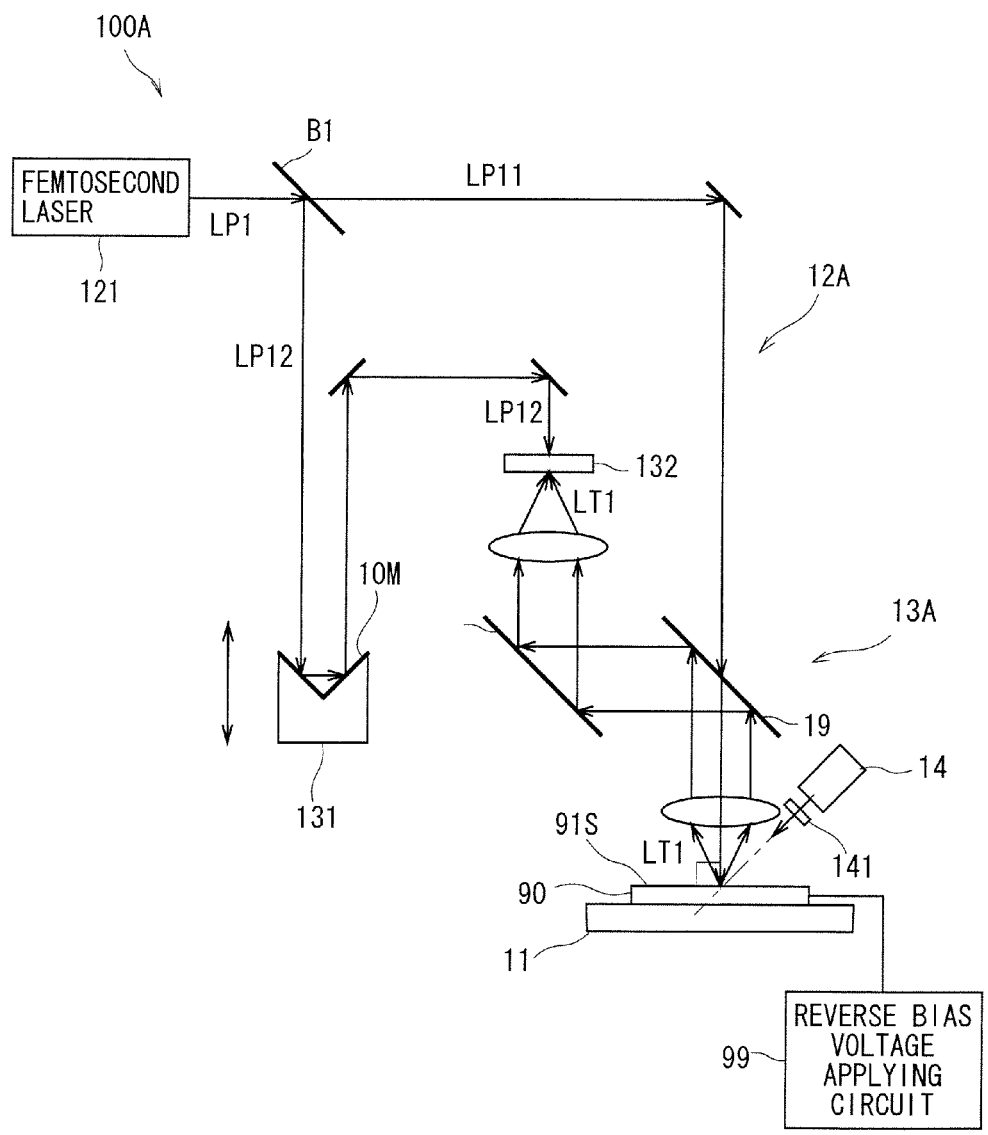
FIG. 12 is a schematic configuration diagram of an irradiation part and a detecting part of an inspection apparatus according to a second preferred embodiment.

FIG. 12 is a schematic configuration diagram of an irradiation part 12A and a detecting part 13A of an inspection apparatus 100A according to a second preferred embodiment. Hereinafter, an element having the same function as that of the constituent of the inspection apparatus 100 of the first preferred embodiment is designated by the same numeral, and the description is omitted.

In the inspection apparatus 100A, the pulsed light LP1 emitted from the femtosecond laser 121 is also split into the pump light LP11 and the probe light LP12 by the beam splitter B1. However, in the second preferred embodiment, the split pump light LP11 is transmitted through a transparent conductive film substrate (ITO) 19, and perpendicularly incident to the light receiving surface 91S of the photovoltaic cell panel 90. The continuous light irradiation part 14 obliquely irradiates the light receiving surface 91S of the photovoltaic cell panel 90 with continuous light CW. In the electromagnetic wave pulses LT1 generated by the irradiation of the pump light LP11, the electromagnetic wave pulse LT1 radiated onto the side of the light receiving surface 91S is reflected by the transparent conductive substrate 19 and incident to the detector 132 through the lens and the like.

The inspection apparatus 100A including the irradiation part 12A and the detecting part 13A can also detect the electromagnetic wave pulse LT1 generated by the irradiation of the pump light LP11. Accordingly, like the inspection apparatus 100 of the first preferred embodiment, the inspection apparatus 100A can inspect the photovoltaic cell panel 90 in the non-contact state.

3. Third Preferred Embodiment

Figure 13:
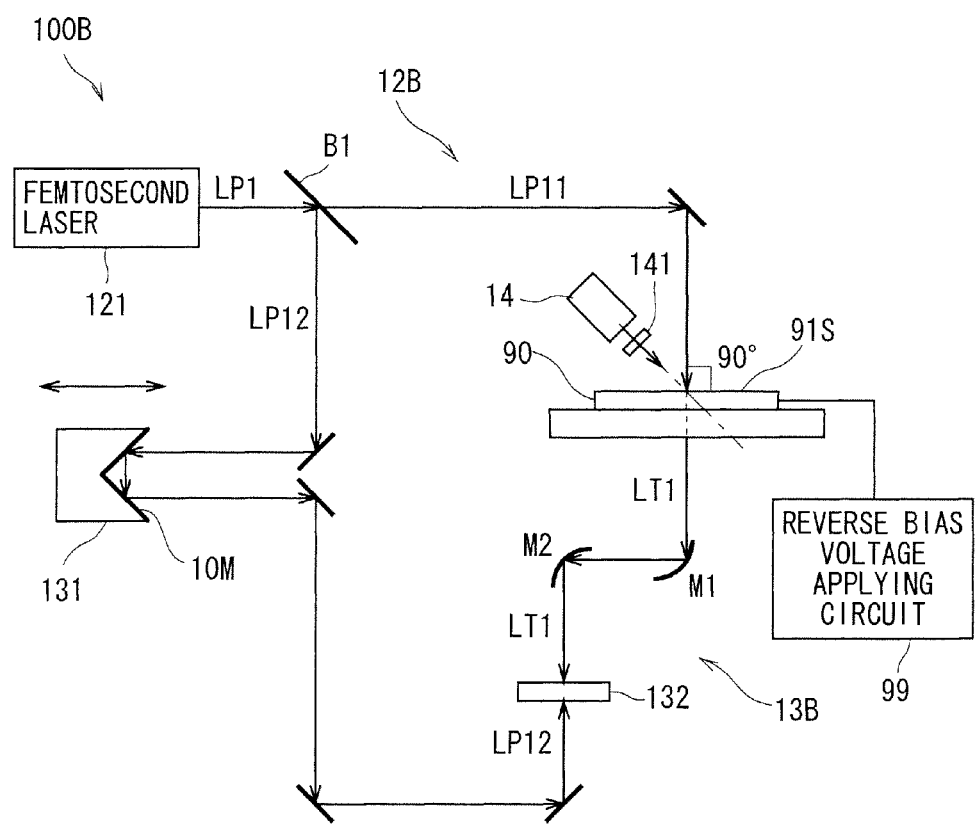
FIG. 13 is a schematic configuration diagram of an irradiation part and a detecting part of an inspection apparatus according to a third preferred embodiment.

FIG. 13 is a schematic configuration diagram of an irradiation part 12B and a detecting part 13B of an inspection apparatus 100B according to a third preferred embodiment. In the inspection apparatus 100B, the pulsed light LP1 emitted from the femtosecond laser 121 is also split into the pump light LP11 and the probe light LP12 by the beam splitter B1. In the third preferred embodiment, the pump light LP11 is perpendicularly incident to the light receiving surface 91S of the photovoltaic cell panel 90. The continuous light irradiation part 14 obliquely irradiates the light receiving surface 91S of the photovoltaic cell panel 90 with the continuous light CW. In the electromagnetic wave pulses LT1 generated by the irradiation of the pulsed light LP11, the electromagnetic wave pulse LT1 output onto (transmitted through) the rear surface side of the photovoltaic cell panel 90 is incident to the detector 132 through the paraboloid mirrors M1 and M2.

The inspection apparatus 100B can also detect the electromagnetic wave pulse LT1 generated by the irradiation of the pump light LP11. Accordingly, like the inspection apparatus 100 of the first preferred embodiment, the inspection apparatus 100B can inspect the photovoltaic cell panel 90 in the non-contact state.

4. Modifications

The preferred embodiments are described above. However, the present invention is not limited to the preferred embodiments, but various modifications can be made.

In the above preferred embodiments, as illustrated in FIG. 3, the pn junction is formed in the photovoltaic cell panel 90 by way of example. Alternatively, the inspection target of the inspection apparatus 100 also includes a photovoltaic cell panel in which what is called a pin junction is formed. In the pin junction, an intrinsic semiconductor layer is sandwiched between a p-type semiconductor layer and an n-type semiconductor layer.

In the above preferred embodiments, the positions where the photovoltaic cell panel 90 is irradiated with the pump light LP11 and the continuous light CW are changed by moving the stage 11. Alternatively, the positions where the photovoltaic cell panel 90 is irradiated with the pump light LP11 and the continuous light CW may optically be changed by controlling an optical element, which is included in the irradiation part 12 or the continuous light irradiation part 14.

The configurations of the above preferred embodiments and modifications may properly be combined or eliminated within a consistent range.

While the invention has been shown and described in detail, the foregoing description is in all aspects illustrative and not restrictive. It is therefore understood that numerous modifications and variations can be devised without departing from the scope of the invention.

What is claimed is:

1. An inspection apparatus that inspects a photo device, the inspection apparatus comprising:
    an irradiation part that irradiates said photo device with pulsed light emitted from a femtosecond laser;
    a detecting part that detects an electromagnetic wave, which is generated from said photo device according to the irradiation of said pulsed light;
    a continuous light irradiation part that irradiates a portion, which is irradiated with said pulsed light in said photo device, with continuous light; and
    an irradiation condition changing part that changes an irradiation diameter of said continuous light.

2. The inspection apparatus according to claim 1, wherein said irradiation condition changing part changes an intensity of said continuous light.

3. The inspection apparatus according to claim 1, wherein said continuous light includes pieces of light having a plurality of wavelengths different from each other.

4. The inspection apparatus according to claim 3, wherein said photo device is a photovoltaic cell, and said continuous light includes artificial sunlight.

5. The inspection apparatus according to claim 1, wherein said continuous light is a laser beam having a single wavelength.

6. The inspection apparatus according to claim 1, further comprising a reverse bias voltage applying part that applies a voltage to put said photo device into a reverse bias state.

7. The inspection apparatus according to claim 1, wherein said continuous light irradiation part is constructed by a semiconductor laser, an LED or a combination thereof.

8. An inspection method for inspecting a photo device, comprising the steps of:
    irradiating said photo device with pulsed light emitted from a femtosecond laser;
    detecting an electromagnetic wave, which is generated from said photo device by the irradiation of said pulsed light;
    irradiating a portion, which is irradiated with said pulsed light in said photo device, with continuous light; and
    changing an irradiation diameter of said continuous light.

9. The inspection method according to claim 8, further comprising the step of changing an intensity of said continuous light.

10. The inspection method according to claim 8, wherein said continuous light includes pieces of light having a plurality of wavelengths different from each other.

11. The inspection method according to claim 10, wherein said photo device is a photovoltaic cell, and said continuous light includes artificial sunlight.

12. The inspection method according to claim 8, wherein said continuous light is a laser beam having a single wavelength.

13. The inspection method according to claim 8, wherein the step of irradiating the portion includes applying a reverse bias voltage to put said photo device into a reverse bias state.

* * * * *

UNITED STATES PATENT AND TRADEMARK OFFICE
CERTIFICATE OF CORRECTION

PATENT NO. : 9,103,870 B2  
APPLICATION NO. : 13/744987  
DATED : August 11, 2015  
INVENTOR(S) : Hidetoshi Nakanishi et al.

Page 1 of 1

It is certified that error appears in the above-identified patent and that said Letters Patent is hereby corrected as shown below:

On the title page item (73), change "SCREEN HOLDINGS CO., LTD., Kyoto, (JP)" to
--SCREEN HOLDINGS CO., LTD., Kyoto, (JP) and OSAKA UNIVERSITY, Osaka (JP)--.

Signed and Sealed this  
Tenth Day of November, 2015

Michelle K. Lee  
*Director of the United States Patent and Trademark Office*